United States Patent [19]

Hoy

[11] Patent Number: 6,024,980
[45] Date of Patent: Feb. 15, 2000

[54] MULTIPHASE SOFT GELATIN DOSAGE FORM

[75] Inventor: Michael R. Hoy, Sellersville, Pa.

[73] Assignee: McNeil-PPC, Inc., Skillman, N.J.

[21] Appl. No.: 08/671,979

[22] Filed: Jun. 28, 1996

[51] Int. Cl.⁷ ........................................................ A61K 9/48
[52] U.S. Cl. ........................... 424/456; 424/451; 424/452; 424/454; 424/455; 514/772.3; 514/781
[58] Field of Search ..................................... 424/451, 452, 424/455, 456, 457, 454

[56] References Cited

U.S. PATENT DOCUMENTS

| | | | |
|---|---|---|---|
| 4,486,412 | 12/1984 | Shah et al. | 424/156 |
| 4,690,822 | 9/1987 | Uemura et al. | 424/455 |
| 4,695,466 | 9/1987 | Morishita et al. | 424/456 |
| 4,708,834 | 11/1987 | Cohen et al. | 264/4.3 |
| 4,734,284 | 3/1988 | Terada et al. | 424/455 |
| 4,772,472 | 9/1988 | Schonmann et al. | 424/451 |
| 4,894,978 | 1/1990 | Schonmann et al. | 53/560 |
| 4,935,243 | 6/1990 | Borkan et al. | 424/441 |
| 4,956,184 | 9/1990 | Kross | 424/661 |
| 5,071,643 | 12/1991 | Yu et al. | 514/570 |
| 5,073,384 | 12/1991 | Valentine et al. | 424/274 |
| 5,156,849 | 10/1992 | Byrne et al. | 424/451 |
| 5,209,978 | 5/1993 | Kosaka et al. | 428/402.2 |
| 5,501,857 | 3/1996 | Zimmer | 424/438 |
| 5,725,846 | 3/1998 | Vu et al. | 424/65 |

FOREIGN PATENT DOCUMENTS

| | | |
|---|---|---|
| 0 211 079 A1 | 2/1987 | European Pat. Off. . |
| 0 308 637 A1 | 4/1988 | European Pat. Off. . |
| 0 571 217 | 11/1993 | European Pat. Off. . |
| 2 624 012 | 6/1989 | France . |
| 203477 | 1/1991 | Hungary . |
| 62-40058 | 8/1987 | Japan . |
| 91/07950 | 6/1991 | WIPO . |
| 92/06680 | 4/1992 | WIPO . |
| 95/01166 | 1/1995 | WIPO . |

OTHER PUBLICATIONS

Derwent Abstract WPI Acc. No. 89–069518/198910, Apr. 1988.

*Remington's Pharmaceutical Science*, 18th Ed., Chapter 83, pp. 1539–1540 (1990).

*Drug Development and Industrial Pharmacy*, 15 (5), pp. 691–704 (1989).

*Primary Examiner*—James M. Spear
*Attorney, Agent, or Firm*—Bernard Plantz

[57] ABSTRACT

The present invention relates to a dosage form containing a common enclosure of polymeric material. The enclosure contains multiple phases of semi-solid fill materials containing active ingredients.

25 Claims, No Drawings

MULTIPHASE SOFT GELATIN DOSAGE FORM

This invention is also related to commonly assigned U.S. patent application Ser. No. 08/366,945, filed Dec. 29, 1994, entitled "Soft Gelatin Pharmaceutical Dosage Form"; Ser. No. 08/366,271, filed Dec. 29, 1994, U.S. Pat. No. 5,660,859, entitled "Gelling Agent for Polyethylene Glycol"; Ser. No. 08/671,991, filed Jun. 28, 1996, entitled "Fill Material for Soft Gelatin Pharmaceutical Dosage Form"; and Ser. No. 08/671,988, filed Jun. 28, 1996, U.S. Pat. No. 5,908,636 entitled "Fill Material for Soft Gelatin Pharmaceutical Dosage Form Containing an Antiflatulent," all of which are hereby incorporated by reference.

FIELD OF THE INVENTION

The present invention relates to a gelatin capsule having discrete phases or regions of a semi-solid fill material containing an active ingredient.

BACKGROUND OF THE INVENTION

In recent years soft gelatin or soft elastic gelatin capsules have become a popular dosage form for the oral delivery of therapeutic agents, especially over-the-counter pharmaceuticals. These capsules are typically filled with a liquid containing the active ingredient. Because of their soft, elastic character, some patients view these capsules as easier to swallow than conventional tablets or hard gelatin capsules. Since the dosage form is generally swallowed, it is not necessary to flavor or otherwise mask the often unpleasant taste of the pharmaceutical. Soft gelatin capsules are also preferred to bulk liquids because they are easier to transport and they avoid the need for the patient to measure a prescribed amount of the liquid before dosing.

The fill material used in a soft gelatin capsule generally contains a pharmaceutical dissolved or dispersed in a carrier that is compatible with the capsule wall. In addition to liquids, U.S. Pat. No. 4,935,243 to L. Borkan et al. suggests that the fill material may take the form of a semi-solid, solid, or gel. Conventional tablets or pellets containing an active ingredient are examples of solid fill materials that may be encapsulated within a soft gelatin capsule.

Semi-solid (dispersion) fill material are discussed in U.S. Pat. No. 4,486,412 to D. Shah et al. A fill material containing an orally-administered antacid salt that is dispersed in a water-free, liquid carrier containing a major proportion of one or more polyalkylene glycols and a minor proportion of a $C_2$–$C_5$ polyol, such as propylene glycol or glycerin. The carrier forms a stable dispersion of the antacid salt and coats the antacid particles, thereby rendering them non-reactive with the soft gelatin capsule wall. The dispersion may also contain a polysiloxane flatulence-relieving agent, such as simethicone, as an optional ingredients. Such optional ingredients comprise about 0–5% by weight of the total dispersion.

U.S. Pat. No. 4,708,834 to Cohen et al. suggests a controlled release pharmaceutical dosage form comprising a soft gelatin capsule that encloses a water-soluble or dispersible gelled polymer matrix. The fill material comprises an aqueous solution or dispersion of a polysaccharide gum, the pharmaceutical active and, optionally, an alcohol. The liquid fill is introduced into a soft gelatin capsule that contains a cationic gelling agent, which gels the liquid fill after it has been incorporated into the capsule shell. The alcohol used in the fill includes liquid polyethylene glycols, lower alkanols, $C_2$–$C_4$ polyols and mixtures thereof.

U.S. Pat. No. 5,071,643 to M. Yu et al. also discusses the use of polyethylene glycols (PEG) as a fill material in soft gelatin dosage forms. PEGs having an average molecular weight between 400–600 are preferred for liquid fills, between 800–10,000 for semi-solid fills and between 10,000–100,000 for solid fills.

*Remington's Pharmaceutical Sciences*, 18th ed, Chapter 83, pp. 1539–40 (1990), reports that gelling agents used to make gels for pharmaceutical and cosmetic products, include sodium alginate and triethanolamine.

PCT Publication No. WO 91/07950 describes a soft or two-piece hard gelatin capsule shell containing benzodiazepine dissolved or suspended in a gel. The gel contains by weight at least 63% of polyethylene glycol 600, at least 4% of polyethylene glycol 4000 or 6000, and at least 21% of polyethylene glycol 600–4000. This gel fill cannot be expelled with a syringe at ambient temperature and therefore avoids the reported abuse of liquid filled capsules by intravenous drug abusers.

Antiflatulents are typically incorporated into compressible tablets by mixing the oily-like substances, such as simethicone, with standard tableting excipients prior to tableting. U.S. Pat. No. 5,073,384 to Valentine et al. describes a composition suitable for tableting comprising simethicone and a water soluble, maltodextrin agglomerate. The resulting combinate is reported to be free flowing and possess defoaming activity.

Hungarian Patent No. 203,477, published Jan. 28, 1991, describes an antiflatulent, solid dispersion containing poly (dimethylsiloxane) as a dispersed phase in a water soluble carrier. The dispersion also contains a lattice-forming and/or a crosslinking, viscosity-increasing macromolecular auxiliary substance such as polyvinyl chloride, polyacrylic acid, or polyvinylpyrrolidone and/or inorganic solidifying agent, such as tricalcium phosphate, calcium sulfate hemihydrate or calcium hydrogen phosphate. Example 1 reports a solid mass containing 60 g of polyethylene glycol 6000, 15 g of polyvinyl chloride and 25 g of activated dimethicone (simethicone) that can be ground and filled into solid gelatin capsules or made into tablets.

French Patent Application No. 2,624,012, published Jun. 9, 1989, relates to a soft gelatin capsule containing a suspension or solution of chloral hydrate in a high viscosity inert vehicle. Suitable vehicles for use in the capsule include oily solvents of mineral or vegetable oil, such as olive oil, peanut oil, paraffin oil, vaseline oil or mixtures of several oils; a liquid silicone such as dimethicone or simethicone; a glycol polymer such as polyethylene glycol 600, 800 or 1200; and a glycol such as ethylene glycol, propylene glycol or glycerol.

Simethicone has been incorporated in syrup or clear base liquid oral formulations. A. Banga et al. in "Incorporation of Simethicone into Syrup or Clear Base Liquid Orals," *Drug Development and Industrial Pharmacy*, 15(5), pgs. 691–704 (1989) describes a variety of vehicles for simethicone, but reports the best results were obtained with neutralized CARBOPOL® (carboxypolymethylene) resins in combination with glycerin and propylene glycol.

U.S. Pat. Nos. 4,772,472 and 4,894,978 to Schonmann et al. relate to gelatin capsules having at least two equal active ingredients in two different carrier substances or at least two different active ingredients in two equal carrier substances. The carrier substances are provided in the capsule in a layered side-by-side relationship without a partition or separating wall.

A need exists for a gelatin capsule containing multiple phases or regions of semi-solid fill materials containing therapeutically effective amount of a pharmaceutical. At least one of the regions or phases should be substantially translucent so as to provide a distinct visual appearance. The semi-solid fill materials should be sufficiently viscous so as to prevent them from being readily expelled from the capsule shell with a syringe to minimize the potential for product tampering.

SUMMARY OF THE INVENTION

The present invention provides a dosage form having a common enclosure of a polymeric material. The enclosure contains first and second phases which are disposed in discreet regions of the enclosure and are in contact with each other at at least one interface. The first and second phases each contain a semi-solid fill material, with at least one phase containing an active ingredient. The first and second phases differ in composition and at least one of the phases has a turbidity less than 1300 NTU (Nephelometric Turbidity Unit).

In a further embodiment of the present invention, the common enclosure of polymeric material is a soft gelatin capsule containing a first phase which is substantially translucent and a second phase which opaque, which results in a dosage form having a distinct appearance.

In a further embodiment of the present invention, the semi-solids forming the first and second phases are sufficiently viscous so that they cannot be expelled at room temperature from the dosage form with a syringe, preferably having a 16 gauge or smaller needle.

DETAILED DESCRIPTION OF THE PREFERRED EMBODIMENTS

The present invention relates to a pharmaceutical dosage form containing a common enclosure of polymeric material. The enclosure may take the form of a soft gelatin capsule or a two-piece hard gelatin capsule. The enclosure of polymeric material contains multiple phases which are distinctive on a qualitative and/or quantitative compositional basis. As used in the present invention, phase is meant to define a semi-solid fill material, which may contain an active ingredient. The phases may be disposed in the enclosure in a variety of patterns or sequences. Generally, the phases are in a side-by-side layered arrangement wherein they are in contact with each other at at least one interface. Alternatively, the phases may be randomly disposed within the enclosure in a non-layered or marbelized arrangement.

The composition of each phase is dependent upon the intended use of the dosage form. The phase may contain virtually any active ingredient such as pharmaceuticals, vitamins and minerals. These active(s) are present in the phases in therapeutically effect amounts, which are amounts which produce the desired therapeutic response upon oral administration, and can be readily determined by one skilled in the art. In determining such amounts, the particular compound being administered, the bioavailability characteristics of the compound, the dosage regimen, the age and weight of the patient and other factors must be considered. Since the phases are in the form of a semi-solid, two adjacent phases may contain active ingredients which are incompatible with each other since there is minimal diffusion between the layers. The phases may also contain active ingredients which are coated or otherwise processed to provide a delayed or sustained release. For instance, an analgesic in a ready release form may be formulated in a first phase whereas the same analgesic with a delayed release coating is used in the second phase. Upon administration, this dosage form provides a sustained or extended release profile. In addition to coatings which affect the rate of dissolution, enteric or other coatings may be employed to control the location of the release of the active ingredient with the body.

For aesthetic reasons, it may be desirable to formulate one or more of the phases so that it is free of any active ingredient. This placebo phase may then be formulated to give the desired visual appearance, such as translucent, opaque or colored.

As used in the present invention, a semi-solid is a system of at least two constituents consisting of a condensed mass enclosing and interpenetrated by a liquid. The semi-solid fill materials used in the phases of the present invention are sufficiently viscous so that an appreciable amount, less than about 1, preferably less than about 0.5, gram cannot be expelled at room temperature with a syringe having a 16 gauge or smaller needle. The visual appearance of the phases may also be controlled depending upon the formulation used to form the semi-solid fill material. The dosage form may contain both an opaque and a translucent phase or two translucent phases. If two translucent phases are employed, colorants may be added to form regions having different colors. In a preferred form of the present invention, the multi-phase dosage form has both opaque and translucent phases.

In a still further preferred form of the present invention, the dosage form contains a first opaque phase containing an antiflatulent, such as simethicone or dimethicone, and a substantially translucent second phase containing an antidiarrheal, such as loperamide HCl. Since the active ingredients are disposed in distinct phases, the deleterious effect of simethicone on a dissolution profile of loperamide HCl is avoided. Specifically, this problem is overcome without the use of a barrier layer as set forth in commonly assigned European Patent Publication No. 0 571 217, published Nov. 24, 1993.

The following illustrate translucent and opaque phases that may be employed in the present invention.

Translucent Phase

The translucent semi-solid of the present invention contains a liquid polyalkylene glycol having an average molecular weight of about 600 or less. The polyalkylene glycol serves as a solvent for the pharmaceutical. A suitable polyalkylene glycol is polyethylene glycol. The polyethylene glycols preferably have an average molecular weight of about 200 to about 600, and most preferably about 300 to about 400. The translucent semi-solid generally comprises by weight about 35 to about 99, preferably about 85 to 99, percent solvent. Unless otherwise stated, the percentages recited herein are by weight of the total weight of the translucent semi-solid fill material, i.e., both the semi-solid and active ingredient.

The translucent semi-solid is formed by thickening the solvent with cellulose ethers. A suitable cellulose ether is hydroxypropyl cellulose. Preferably the thickening agent is hydroxypropyl cellulose, NF having a molecular weight of about 80,000 to about 1,150,000. Hydroxypropyl cellulose, NF is commercially available from Aqualon, Inc. under the tradename KLUCEL®, and the preferred grades are KLUCEL GF, MF and HF having a molecular weight range of about 370,000 to about 1,150,000. Lower molecular weight hydroxypropyl cellulose, including KLUCEL EF, LF and JF, having a range of about 80,000 to about 140,000 may also be used, but generally at higher concentrations than the higher molecular weight grades.

In a preferred embodiment, the thickening agent is employed in an amount effective to form a semi-solid that is substantially translucent and is sufficiently viscous so that it cannot be expelled at room temperature with a syringe having an 16 gauge or smaller needle. Generally the semi-solid contains by weight from about 0.10 to about 10, preferably about 0.25 to about 3.5, percent of one or more of the cellulose ethers.

In addition to the liquid polyalkylene glycol, the semi-solid may contain solubilizing agents to enhance the solubility or dispersibility of the active ingredient in the semi-solid. Suitable agents include propylene glycol, glycerin, ethanol, N-methyl-2-pyrrolidone, dimethyl isosorbide, povidone (PVP), poloxamer, other pharmaceutically acceptable surfactants and mixtures thereof. A preferred poloxamer (poly(oxyethylene)-poly(oxypropylene)copolymer) is Poloxamer 124, available from BASF under the tradename PLURONIC L 44. The translucent semi-solid generally comprises 0 to about 8, preferably 0 to about 6, percent of the solubilizing agent. In addition, the semi-solid may contain 0 to about 10 percent water.

If acetaminophen, famotidine, ranitidine, cimetidine or other readily oxidizable substance is used as the active ingredient, it may desirable to include an antioxidant to eliminate degradation or discoloration, such as "pinking" of acetaminophen.

The pharmaceutical active(s) is present in the translucent phase of the dosage form in a therapeutically effective amount. Pharmaceuticals suitable for use in the translucent phase include acetaminophen, famotidine, chlorpheniramine, pseudoephedrine, dextromethorphan, diphenhydramine, brompheniramine, clemastine, phenylpropanolamine, terfenadine, astemizole, loratadine, loperamide, loperamide-N-oxide, ranitidine, cimetidine, tramadol, cisapride, acetylsalicylic acid, doxylamine succinate, pharmaceutically acceptable salts thereof and mixtures thereof. Generally, the pharmaceutical comprises about 0.1 to about 40, preferably about 0.2 to about 30, percent by weight of the total translucent semi-solid composition.

Various other pharmaceutically acceptable excipients may be included in the translucent semi-solid fill material, such as preservatives, e.g., methyl- or propylparaben, coloring agents, flavoring agents, lubricants, flow-enhancers, antioxidants, surfactants, plasticizers, filling aids and other compounds, agents and components which produce an appealing final product. The translucent semi-solid fill material generally has a turbidity less than about 1300, preferably less than about 200, NTU.

In a preferred embodiment, a translucent fill containing about 180 mg/mL acetaminophen, comprises by weight about 10 to about 40 percent acetaminophen, about 40 to about 90 percent polyethylene glycol having an average molecular weight of about 400 (PEG 400), 0 to about 8 percent water, from 0 to about 8 percent propylene glycol, and from about 2 to about 8 percent hydroxypropyl cellulose.

In a still further preferred embodiment, a translucent fill containing from 10–40 mg/mL famotidine, comprises by weight about 0.5 to about 4 percent famotidine, from about 60 to about 99 percent PEG 400, from 0 to about 8 percent water, from 0 to about 8 percent, propylene glycol, and from about 2 to about 8 percent hydroxypropyl cellulose.

In a still further preferred embodiment a translucent fill containing 17 mg/mL loperamide HCl, comprises by weight about 1 to about 3 percent loperamide HCl, from about 92 to about 99 percent PEG 400, from 0 to about 8 percent water, from 0 to about 8 percent propylene glycol, and from about 0.5 to about 3 percent hydroxypropyl cellulose.

Opaque Phase

The opaque semi-solid of the present invention also contains a polyalkylene glycol. Suitable polyalkylene glycols include polyethylene glycol (PEG) having an average molecular weight of about 400 to about 20,000, preferably about 400 to about 3350. The opaque semi-solid generally comprises by weight about 30 to about 70, preferably about 40 to about 60, percent of the polyalkylene glycol. Unless otherwise stated, the percentages recited herein are by weight of the total weight of the opaque semi-solid fill material, i.e., both the semi-solid and the antiflatulent.

Blends of PEGs of varying molecular weights may also be used in the opaque semi-solid fill material of the present invention. The blends will generally contain low molecular weight PEGs having an average molecular weight of about 600 or less mixed with high molecular weight PEGs having an average molecular weight of greater than about 600 to about 10,000 in amounts that produce a semi-solid. Preferably, such blends contain about 0.25 to about 5 percent of the low molecular weight PEG and about 45 to about 50 percent of the high molecular weight PEG.

In addition to the liquid polyalkylene glycol, the opaque semi-solid may contain one or more auxiliary semi-solid forming agents in the amount shown (% by wt. of semi-solid):

| %         | Component                                   |
|-----------|---------------------------------------------|
| 0.05–10   | Propylene Glycol                            |
| 0.05–15   | Plurol Stearic (polyglyceryl-6-distearate)  |

| % | Component |
|---|---|
| 0.05–10 | Peceol (glycerol oleate) |
| 0.05–5 | Hydroxypropyl Cellulose, NF |

The opaque semi-solid may contain 0 to about 10 percent water.

The antiflatulent is present in the opaque phase of the dosage form in a therapeutically effective amount. Antiflatulents suitable for use in the invention include simethicone and dimethicone. Generally, the antiflatulent comprises about 30 to about 70, preferably about 40 to about 60, percent by weight of the total semi-solid fill material. The defoaming time of semi-solid fill material containing the antiflatulent is preferably less than about 15, preferable less than about 9, seconds.

Various other pharmaceutically acceptable excipients may be included in the opaque semi-solid fill material, such as preservatives, e.g., methyl- or propylparaben, coloring agents, flavoring agents, lubricants, flow-enhancers, antioxidants, humectants (glycerin), surfactants, plasticizers, filling aids and other compounds, agents and components which produce an appealing final product.

In a preferred embodiment, an opaque semi-solid fill containing 547 mg/mL simethicone, comprises by weight about 40 to about 60 percent simethicone, about 1 to about 3 percent liquid polyethylene glycol having an average molecular weight of about 300 to about 400 and about 40 to about 60 percent solid polyethylene glycol having an average molecular weight of about 1450 to about 4600. This semi-solid preferably has a viscosity of about 900,000 to about 1,000,000 cp at 25° C., a defoam time of less than about 8 seconds (as measured by the USP method described below) and a syringeability of less than 0.5 gram (as measured by the method described below).

The semi-solid fill materials of the present invention may be used in commercially available soft gelatin capsules, such as those commercially available from R. P. Scherer or Banner Pharmacaps. Various sizes, shapes, and colors can be used to accommodate different levels of active ingredients. The walls of the capsules have a substantially translucent or clear appearance. When the opaque fill material is introduced into the capsule and forms a semi-solid, the corresponding region of resulting dosage form has a white opaque appearance, or colorants may be added to achieve any desired color. When the translucent fill material is introduced into the capsule and forms a semi-solid, the corresponding region of the dosage form has an elegant, translucent or clear appearance. The translucent fill may also be colored or tinted with coloring agents.

The fill materials are heated before they are loaded into the capsule because they are highly viscous at temperatures below 40° C. Air-filled soft gelatin capsules can be hand filled with a syringe. The hot liquid fill is loaded into a syringe. The needle on the syringe is used to puncture one end of the soft gelatin capsule so that the appropriate amount of fill material may be injected by hand. This procedure is repeated for each semi-solid fill material, so that the resulting dosage form has discrete layers or phases in a side-by-side relationship. Alternatively, the two or more distinct semi-solid fill materials may be introduced randomly to produce a random pattern of semi-solid phases. The capsule with fill materials is allowed to cool.

The fill material may also be introduced into the soft gelatin capsule using encapsulation equipment and techniques known in the art, such as that described in U.S. Pat. Nos. 4,772,472 and 4,894,978 to Schonmann et al., which are hereby incorporated by reference. As previously described with the hand-filling technique, the fill must be maintained at above about 40° C. during the filling operation so that it readily flows into the capsule. Therefore, the fill can be stored in a jacketed vessel and transported through a thermostatically controlled feeding tube to the encapsulation equipment.

Specific embodiments of the present invention are illustrated by way of the following examples. This invention is not confined to the specific limitations set forth in these examples, but rather to the scope of the appended claims. Unless otherwise stated, the percentages and ratios given below are by weight of the total composition of the semi-solid fill.

Viscosity was measured in the following examples using a Rheometrics Fluids Spectrometer 8400 at 25° C. Using a 25 mm parallel plate and a constant strain of 10%, frequency sweeps were performed. Viscosity was recorded at a frequency of 1.0 radian per second.

Defoaming testing in the following examples was carried out using United States Pharmacopeia 23 rev., The National Formulary 18 ed. specifications and procedures. The foaming solution consisted of 1% octoxynal-9 and 0.0005% FD&C Blue #1 in water. The testing equipment comprised a weight action shaker with radius set at 13.3±0.4 cm (measured from center of shaft to center of bottle) An equivalent of 20 mg simethicone was transferred into a jar containing 100 ml foaming solution, previously heated to 37° C. The jar was capped and shaken at an arc of 10 degrees at a frequency of 300±30 strokes/minute for 10 seconds. The time taken for a portion of foam-free liquid to appear was recorded. The USP limit being NMT 15 seconds.

Syringeability testing was performed in the following examples to measure the ability to syringe each formulation within a controlled time period. This test was used as a gauge of tamper resistance. 10 cc syringes were used with 16 gauge needles, 1.5 inches in length. The syringe was placed in the formulation, the plunger was pulled up and held for 10 seconds. The weight of the fill material pulled into the syringe was recorded.

The turbidity of the translucent fill materials described in the following examples was measured using a Hach Ratio/XR Turbidimeter. The United States Pharmacopeia defines turbidance as the light-scattering effect of suspended particles and turbidity as the measure of the decrease in the incident beam intensity per unit length of a given suspension. This instrument measures turbidity within a range of 0.00 to 2000 NTU. As a point of reference, the turbidity of water is zero. Samples of the fill materials, approximately 8mL, were transferred to Fisher Brand 13×100 mm culture tubes immediately after manufacture. The fill material samples were stored at ambient room temperature since they were made several days in advance. The outer surface of each of the sample culture tubes was treated with silicone oil just prior to measuring the turbidity. The turbidity of the samples was measured at ambient room temperature. The turbidity of two sample tubes of each fill material was measured and the average of the results is reported.

Dissolution testing was performed in the following examples using USP type I baskets set at 100 rpm. and an acetate buffer (pH 4.7) with pepsin as the medium. Volume was 500 mL, the USP limits are NMT 80% in 30 minutes. An amount of the formulation equivalent to a 4.0 mg. dose of loperamide HCl was tested on a soft gelatine capsule cut in half.

EXAMPLE 1

This Example provides a comparison of the PEG blends similar to those described in PCT Publication WO 91/07950. The following blends were prepared:

| | Amount (% w/w) | |
|---|---|---|
| Component | Sample A | Sample B |
| PEG 600 | 64.40 | 64.40 |
| PEG 1450 | 26.20 | 26.20 |
| PEG 3500 | — | 4.20 |
| PEG 8000 | 4.20 | — |
| Glycerol | 5.20 | 5.20 |

The samples were prepared as follows:

1) Weigh PEGs and glycerol.
2) Place mixture on preheated hot plate set to highest setting. Mix with heat (approximately 75° C.) until a clear solution is obtained.
3) Remove mixture from heat and mixing. Sonicate with heat temp set=69° C. Upon cooling to RT to form a gel, both Samples had an opaque white appearance with a turbidity exceeding 2000 NTU.

EXAMPLE 2

This Example discloses a translucent semi-solid fill material of the present invention containing about 180 mg/mL of acetaminophen. The fill contains:

| Component | Amount (% w/w) |
|---|---|
| Acetaminophen | 29.0 |
| PEG-400 (400 MW) | 66.7 |
| Hydroxypropyl Cellulose (KLUCEL GF;300,000 MW) | 4.3 |

The sample is prepared as follows:

1) PEG-400 is heated to 110–120° C. and the acetaminophen is slowly added while stirring.
2) After the acetaminophen goes into solution, the hydroxypropyl cellulose is added while stirring.
3) After the resulting mixture appears to be a clear solution, it is allowed to cool to room temperature.

EXAMPLE 3

This Example discloses a translucent semi-solid fill material of the present invention containing 10 mg/mL of famotidine. The fill material contained:

| Component | Amount (% w/w) |
|---|---|
| Famotidine | 1.6 |
| PEG 400 (400 MW) | 91.3 |
| Hydroxypropyl Cellulose (KLUCEL GF;300,000 MW) | 7.1 |

The sample was prepared as follows:

1) PEG-400 was heated to 110–120° C. and the hydroxypropyl cellulose was slowly added while stirring.
2) After the hydroxypropyl cellulose went into solution, the formulation was cooled to about 70° C.
3) The famotidine was added while stirring.
4) After the resulting mixture appeared to be a clear solution, it was allowed to cool to room temperature to give a clear, semi-solid.

The turbidity of the resulting sample was 14.6 NTU.

EXAMPLE 4

This Example discloses translucent semi-solid fill materials of the present invention containing 17 mg/mL of loperamide HCl. The fill materials contained:

| | Amount (% w/w) | |
|---|---|---|
| Component | A | B |
| Hydroxypropyl Cellulose (KLUCEL HF; 1,150,000 MW) | 0.5 | 0.5 |
| Propylene Glycol | — | 6.0 |
| PEG 400 | 98.0 | 92.0 |
| Loperamide HCl | 1.5 | 1.5 |

The samples were prepared as follows:

1) Weigh PEG 400, propylene glycol and hydroxypropyl cellulose into beaker.
2) Mix at high speed on hot plate, set to approx. 120° C., until polymer is completely dissolved.
3) Reduce heat to approx. 70° C. and add loperamide HCl, mix until dissolved.

The resulting formulations were allowed to cool to room temperature to give a clear, semi-solid.

EXAMPLE 5

This Example discloses translucent semi-solid fill materials containing 17 mg/mL of loperamide HCl. The fill materials contained:

| | Amount (% w/w): | |
|---|---|---|
| Component | A | B |
| Hydroxypropyl Cellulose (KLUCEL MF; 850,000 MW) | 3.0 | 3.0 |
| Propylene Glycol | — | 6.0 |
| PEG 400 | 95.5 | 89.5 |
| Loperamide HCl | 1.5 | 1.5 |

The samples were prepared as follows:

1) Weigh PEG 400, propylene glycol and hydroxypropyl cellulose into beaker.

2) Mix at high speed on hot plate, set to approx. 120° C., until polymer is completely dissolved.
3) Reduce heat to approx. 70° C. and add loperamide HCl, mix until dissolved.

The resulting formulations were allowed to cool to a clear, semi-solid.

EXAMPLE 6

This Example discloses a translucent semi-solid fill material containing 17 mg/mL loperamide HCl. The fill material contained:

| Component | Amount (% w/w): |
|---|---|
| Hydroxypropyl Cellulose (KLUCEL HF; 1,150,000 MW) | 1.5 |
| Propylene Glycol | 5.5 |
| PEG 400 | 91.5 |
| Loperamide HCl | 1.5 |

The sample was prepared as follows:
1) Weigh PEG 400, propylene glycol and hydroxypropyl cellulose into beaker.
2) Mix at high speed on hot plate, set to approx. 120° C., until polymer is completely dissolved.
3) Reduce heat to approx. 70° C. and add loperamide HCl, mix until dissolved.

The resulting formulation was allowed to cool to room temperature to give a clear semi-solid.

EXAMPLE 7

This Example discloses a translucent semi-solid fill material containing 17 mg/mL of loperamide HCl.

| Component | Amount (% w/w): |
|---|---|
| Hydroxypropyl Cellulose (KLUCEL MF; 850,000 MW) | 2.7 |
| Propylene Glycol | 5.5 |
| PEG 400 | 90.3 |
| Loperamide HCl | 1.5 |

The sample was prepared as follows:
1) Weigh PEG 400, propylene glycol and hydroxypropyl cellulose into beaker.
2) Mix at high speed on hot plate, set to approx. 120° C., until polymer is completely dissolved.
3) Reduce heat to approx. 70° C. and add loperamide HCl, mix until dissolved.

The resulting formulation was allowed to cool to room temperature to give a clear semi-solid.

The following summarizes the results of the sample testing for Examples 1 and 3–7:

| Example | Syringeability (g) | Clarity (NTU) | Viscosity (cPs) |
|---|---|---|---|
| 1A | — | >2000 | — |
| 1B | — | >2000 | — |
| 3 | — | 14.6 | — |
| 4 | 0.06 | — | 69,810 |
| 5A | 0.08 | 34 | 18,200 |
| 5B | 0.06 | 21 | 87,870 |
| 6 | 0.32 | 5.5 | 78,070 |
| 7 | 0.23 | 10.2 | 156,900 |
| Robitussin ® Liqui-Gels ® | 1.6 | — | — |
| Drixoral ® Cough Liqui-Gels ® | 3.2 | — | — |
| Water | 11.5 | — | — |

EXAMPLE 8

This Example discloses opaque semi-solid fill materials of the present invention containing 547 mg/ml simethicone. The following samples were prepared:

| | Amount (% w/w) | | | | |
|---|---|---|---|---|---|
| Component | A | B | C | D | E |
| PEG 1450 | 50.0 | — | — | — | — |
| PEG 3350 | — | 50.0 | — | — | — |
| PEG 4600 | — | — | 50.0 | — | — |
| PEG 8000 | — | — | — | 50.0 | — |
| PEG 20,000 | — | — | — | — | 50.0 |
| Simethicone (Dow Corning) | 50.0 | 50.0 | 50.0 | 50.0 | 50.0 |

The samples were prepared:
1) Weigh PEG
2) Melt and stir PEG on hot plate set at approx. 80° C. until clear.
3) Add simethicone slowly and stir at high speed for approx. 20 minutes.
4) Remove from heat and allow to cool without stirring.

The resulting samples were opaque semi-solids.

EXAMPLE 9

This Example discloses opaque semi-solid fill materials of the present invention containing 547 mg/ml simethicone. The following samples were prepared:

| | (Amount (% w/w): | | | |
|---|---|---|---|---|
| Component | A | B | C | D |
| PEG 400 | 0.5 | 0.5 | 0.5 | 0.5 |
| PEG 1450 | 49.5 | — | — | — |
| PEG 3350 | — | 49.5 | — | — |
| PEG 4600 | — | — | 49.5 | — |
| PEG 8000 | — | — | — | 49.5 |
| Simethicone (Dow Corning) | 50.0 | 50.0 | 50.0 | 50.0 |

The samples were prepared as follows:
1) Weigh PEGs.
2) Melt and stir PEGs on hot plate set at approx. 80° C. until clear.
3) Add simethicone slowly and stir at high speed for approx. 20 minutes.

4) Remove from heat and allow to cool without stirring. The resulting samples were opaque semi-solids.

EXAMPLE 10

This Example discloses semi-solid fill materials of the present invention containing 547 mg/ml simethicone. The following samples were prepared:

|  | (Amount (% w/w): | | | |
|---|---|---|---|---|
| Component | A | B | C | D |
| PEG 400 | 3.0 | 3.0 | 3.0 | 3.0 |
| PEG 1450 | 47.0 | — | — | — |
| PEG 3350 | — | 47.0 | — | — |
| PEG 4600 | — | — | 47.0 | — |
| PEG 8000 | — | — | — | 47.0 |
| Simethicone (Dow Corning) | 50.0 | 50.0 | 50.0 | 50.0 |

The samples were prepared using the procedure of Example 9. The resulting samples were opaque semi-solids.

EXAMPLE 11

This Example discloses an opaque semi-solid fill material of the present invention containing 547 mg/mL simethicone. The following sample was prepared:

| Component | Amount (% w/w) |
|---|---|
| PEG 400 | 2.5 |
| PEG 3350 | 47.5 |
| Simethicone (Dow Corning) | 50.0 |

The samples were prepared using the procedure of Example 9. The resulting sample was an opaque semi-solid.

The following summarizes the results of the sample testing of Examples 8–11 and simethicone control:

| Example | Syringeability (g) | Defoam Time (Seconds) | Viscosity (cP) |
|---|---|---|---|
| 8A | 0.047 | 11 | 3,009,000 |
| 8B | 0.091 | 5 | 1,420,566 |
| 8C | 0.180 | 9 | 331,700 |
| 8D | 0.216 | 5 | 213,420 |
| 8E | 0.300 | 8 | 9069 |
| 9A | — | — | — |
| 9B | 0.054 | 6 | 2,856,000 |
| 9C | — | — | — |
| 9D | — | — | — |
| 10A | — | — | — |
| 10B | 0.039 | 10 | 301,000 |
| 10C | — | — | — |
| 10D | 0.165 | 7 | 116,350 |
| 11 | 0.347 | 6 | 1,025,633 |
| Simethicone (Dow Corning) | 1.675 | 9 | 612 |

In the event multiple tests were conducted on the same formulation, the data summarized above is an average of the measured values for the formulations. The semi-solids of the present invention have defoam times equal to or faster than the simethicone control. Further, the syringeability of the semi-solids of the present invention was significantly less than the simethicone control and the defoam times were less than or substantially equivalent to the simethicone control.

EXAMPLE 12

This Example discloses a soft gelatin capsule filled with a translucent semi-solid fill material containing 17 mg/mL of loperamide HCl and an opaque semi-solid fill material containing 547 mg/mL simethicone.

Translucent Phase Preparation

| Component | Amount (% w/w): |
|---|---|
| Hydroxypropyl Cellulose (KLUCEL MF; 850,000 MW) | 2.7 |
| Propylene Glycol | 5.5 |
| PEG 400 | 90.3 |
| Loperamide HCl | 1.5 |

The sample was prepared as follows:
1) Weigh PEG 400, propylene glycol and hydroxypropyl cellulose into beaker.
2) Mix at high speed on hot plate, set to approx. 120° C., until polymer was completely dissolved.
3) Reduce heat to approx. 70° C. and add loperamide HCl, mix until dissolved.

The resulting formulation was allowed to cool to room temperature to give a clear semi-solid having a turbidity of approximately 7.0 NTU, a dissolution of approximately 95% loperamide HCl in 30 minutes and a syringeability of approximately 0.40 gram.

Opaque Phase Preparation

| Component | Amount (% w/w) |
|---|---|
| PEG 400 | 2.5 |
| PEG 3350 | 47.5 |
| Simethicone (Dow Corning) | 50.0 |

The sample was prepared as follows:
1) Weigh PEGs.
2) Melt and stir on hot plate set at approx. 80° C.
3) Add simethicone slowly and stir at high speed.
4) Remove from heat and allow to cool.

The resulting formulation was an opaque semi-solid having a defoaming time of approx. 6 seconds and a viscosity of 3,000,000 cP.

Two Phase (Translucent/Opaque) Soft Gelatin Capsule Preparation

The semi-solid fill materials were warmed so that they would each flow and then filled into hydrophobic and hydrophilic soft gelatin capsules as follows:
1) A 10 cc syringe barrel was filled with the opaque simethicone formulation, without the needle.
2) A 16 gauge needle was attached and was placed inside a pre-weighed air-filled soft gelatin capsule.
3) A 125 mg dosage of simethicone was carefully syringed into the air-filled capsule.
4) A second 10 cc syringe barrel was filled with the loperamide HCl formulation without the needle.

5) A 16 gauge needle was attached and was placed inside the simethicone-filled soft gelatin capsule.
6) A 2 mg dosage of loperamide HCl was carefully syringed onto the simethicone layer.
7) The top of the capsule was sealed with a hot iron.

The resulting soft gelatin capsules had a distinct opaque white layer (simethicone) in a side-by-side relationship with a substantially translucent layer (loperamide HCl).

EXAMPLE 13

This Example reports the results of dissolution and defoaming testing conducted on the formulations of Examples 7 and 11 in a side-by-side arrangement and two control formulations. In all tests, the semi-solids were introduced into the testing apparatus without a gelatin capsule shell.

To simulate the multi-phase dosage form of the present invention, the semi-solids of the Examples 7 and 11 were introduced into the testing apparatus in a side-by-side arrangement. The two semi-solids were in contact with each other at at least one interface, but the two formulations were not intermixed. This semi-solid of Example 7 was present in an amount that provided 2 mg of loperamide HCl whereas the semi-solid of Example 11 was present in an amount that provided 125 mg of simethicone.

Two control samples were also prepared. Control A was prepared by mixing an amount of Example 7 that provided 2 mg of loperamide HCl with an amount of Example 11 that provided 125 mg of simethicone. The two semi-solids were then intimately mixed and the resulting mixture was introduced into the testing apparatus. The mixture that was introduced into the apparatus was substantially homogeneous and exhibited no distinct phases or layers of the semi-solids.

Control B was prepared by mixing an amount of the semi-solid of Example 7 that provided 2 mg of loperamide HCl with 125 mg of simethicone oil. The resulting mixture was then introduced into the testing apparatus. The results of the defoaming and dissolution testing are reported below:

| Sample | Percent Loperamide HCl Dissolution | | Defoam Time |
|---|---|---|---|
| | 15 min. | 30 min. | |
| Control A | 59 | 85 | 16 sec. |
| Control B | 3 | 3 | 1 min. |
| Ex. 13 | 75 | 91 | 7 sec. |

As shown by the above data, the use of the semi-solids of the present invention in a side-by-side arrangement provided significantly enhanced loperamide dissolution when compared to an intimate mixture of the two formulations (Control A) or the formulation wherein simethicone oil was mixed with the loperamide HCl semi-solid (Control B). The data also show that the defoam time of the semi-solids of the present invention in a side-by-side arrangement was significantly better than the controls. This Example demonstrates that the formulations of the present invention in a side-by-side arrangement substantially eliminate the deleterious effect that simethicone oil has on the dissolution of loperamide HCl.

Various modifications can be made to the above-described embodiments without departing from the spirit and scope of the present invention.

What is claimed is:

1. A pharmaceutical dosage form, comprising:
   a gelatin capsule shell;
   a first phase comprising a first semi-solid containing a polyalkylene glycol having an average molecular weight of about 600 or less and a cellulose ether in an amount effective to thicken the polyalkylene glycol, a therapeutically effective amount of a first pharmaceutical dissolved or suspended in said first semi-solid and said first semi-solid having a turbidity less than about 1300 NTU;
   a second phase comprising a second semi-solid fill containing a polyalkylene glycol having an average molecular weight of about 400 to about 20,000 and a therapeutically effective amount of a second pharmaceutical disposed in said semi-solid; and
   said first and second phases each disposed in discrete regions of said shell and in contact with each other at at least one interface.

2. The dosage form of claim 1 wherein in said first semi-solid the polyalkylene glycol is polyethylene glycol.

3. The dosage form of claim 1 wherein the turbidity of said first semi-solid is less than about 200 NTU.

4. The dosage form of claim 1 wherein said first semi-solid further comprises propylene glycol.

5. The dosage form of claim 1 wherein said first semi-solid comprises by weight:
   about 35 to about 99 percent of the polyalkylene glycol;
   0 to about 10 percent propylene glycol;
   0 to about 10 percent of water; and
   about 0.1 to about 10 percent of the cellulose ether.

6. The dosage form of claim 5 wherein said first semi-solid comprises polyethylene glycol having an average molecular weight of about 200 to about 600.

7. The dosage form of claim 1 wherein in said first semi-solid the cellulose ether is hydroxypropyl cellulose.

8. The dosage form of claim 7 wherein in said first semi-solid the cellulose ether is hydroxypropyl cellulose having a molecular weight of about 80,000 to about 1,150,000.

9. The dosage form of claim 1 wherein said first pharmaceutical is selected from the group consisting of acetaminophen, famotidine, chlorpheniramine, pseudoephedrine, dextromethorphan, diphenhydramine, brompheniramine, clemastine, phenylpropanolamine, terfenadine, astemizole, loratadine, loperamide, loperamide-N-oxide, ranitidine, cimetidine, tramadol, cisapride, acetylsalicylic acid, doxylamine succinate, pharmaceutically acceptable salts thereof and mixtures thereof.

10. The dosage form of claim 1 wherein said first semi-solid comprises polyethylene glycol having an average molecular weight of about 300 to about 400 and hydroxypropyl cellulose.

11. The composition of claim 10 wherein the first semi-solid comprises by weight:
   about 85 to about 99 percent of polyethylene glycol having an average molecular weight of about 300 to about 400;

0 to about 8 percent propylene glycol; and about 0.25 to about 3.5 percent of a hydroxypropyl cellulose having an average molecular weight of about 300,000 to about 1,200,000.

12. The dosage form of claim 11 wherein said first semi-solid has a viscosity of at least 30,000 centipoise at 25° C.

13. The composition of claim 12 wherein said first semi-solid comprises by weight:

about 1 to about 3 percent loperamide HCl;

about 92 to about 99 percent polyethylene glycol having an average molecular weight of about 400;

0 to about 8 percent water;

0 to about 8 percent propylene glycol; and about 0.5 to about 3 percent hydroxypropyl cellulose.

14. The dosage form of claim 1 wherein in said second semi-solid the polyalkylene glycol is polyethylene glycol.

15. The dosage form of claim 1 wherein said second semi-solid has a viscosity of about 10,000 to about 2,500,000 centipoise at 25° C.

16. The dosage form of claim 1 wherein said second semi-solid further comprises auxiliary semi-solid forming agents selected from the group consisting of propylene glycol, polyglyceryl-6-distearate, glycerol oleate and hydroypropyl cellulose.

17. The dosage form of claim 1 wherein said second semi-solid, comprises by weight:

about 30 to about 70 percent of polyethylene glycol and about 30 to about 70 percent of antiflatulent.

18. The dosage form of claim 1 wherein said second semi-solid comprises by weight about 0.25 to about 5 percent of a polyethylene glycol having an average molecular weight of about 600 or less and about 45 to about 50 percent of a polyethylene glycol having an average molecular weight of greater than about 600 to about 10,000.

19. The dosage form of claim 1 wherein said second semi-solid comprises an antiflatulent and has a defoam time of less than about 15 seconds.

20. The dosage form of claim 1 wherein said second semi-solid has a syringeability of less than about 0.5 gram.

21. The dosage form of claim 1 wherein in said second semi-solid the pharmaceutical is selected from the group consisting of simethicone and dimethicone.

22. The dosage form of claim 1, wherein said second semi-solid comprises by weight:

about 40 to about 60 percent of polyethylene glycol having an average molecular weight of about 400 to about 3350 and about 40 to about 60 percent of simethicone.

23. The dosage form of claim 22 wherein said second semi-solid has a viscosity of about 400,000 to about 2,000,000 centipoise at 25° C.

24. The dosage form of claim 1 wherein said second semi-solid comprises by weight:

about 40 to about 60 percent simethicone;

about 1 to about 3 percent polyethylene glycol having an average molecular weight of about 300 to about 400; and about 40 to about 60 percent polyethylene glycol having an average molecular weight of about 1450 to about 4600.

25. The dosage form of claim 24 wherein said second semi-solid has a viscosity of about 900,000 to about 1,000,000 centipoise at 25° C., a defoam time of less than about 8 seconds and a syringeability of less than about 0.5 gram.

* * * * *